(12) United States Patent
Ho (10) Patent No.: US 6,236,429 B1
(45) Date of Patent: May 22, 2001

(54) VISUALIZATION SYSTEM AND METHOD FOR A WEB INSPECTION ASSEMBLY

(75) Inventor: Morris D. Ho, Lafayette, CA (US)

(73) Assignee: Webview, Inc., Dillon Beach, CA (US)

( * ) Notice: Subject to any disclaimer, the term of this patent is extended or adjusted under 35 U.S.C. 154(b) by 0 days.

(21) Appl. No.: 09/012,342

(22) Filed: Jan. 23, 1998

(51) Int. Cl.[7] ................................................. H04N 7/18
(52) U.S. Cl. ................... 348/88; 250/559.05; 356/238.2; 382/141; 348/125; 348/128
(58) Field of Search ........................... 348/88, 125, 128; 382/141; 250/559.01, 559.04, 559.05, 559.06, 559.07; 356/237.1, 238.1, 238.2, 238.3

(56) References Cited

U.S. PATENT DOCUMENTS

| | | | |
|---|---|---|---|
| 3,618,063 | 11/1971 | Johnson | 340/259 |
| 3,779,649 | 12/1973 | Bertoya et al. | 356/200 |
| 3,835,332 | 9/1974 | Bridges | 250/563 |
| 3,843,890 | 10/1974 | Anthony, Jr. et al. | 250/563 |
| 3,958,127 | 5/1976 | Faulhaber et al. | 250/563 |
| 4,166,541 | 9/1979 | Smith, Jr. | 209/587 |
| 4,170,419 | 10/1979 | Van Tyne et al. | 356/431 |
| 4,173,441 | 11/1979 | Wolf | 356/431 |
| 4,232,336 | 11/1980 | Henry | 358/106 |
| 4,237,539 | 12/1980 | Piovoso et al. | 364/552 |
| 4,240,110 | 12/1980 | Henry | 358/107 |
| 4,538,915 | 9/1985 | Faulhaber | 356/431 |
| 4,670,659 | 6/1987 | Loose | 250/560 |
| 4,714,340 | 12/1987 | Stillwagon | 356/23 |
| 4,845,356 | 7/1989 | Baker | 250/225 |
| 4,877,323 | 10/1989 | Stillwagon | 356/23 |
| 5,055,679 | 10/1991 | Ninomiya et al. | 250/306 |
| 5,239,376 | * 8/1993 | Dittmann et al. | 348/88 |
| 5,301,129 | 4/1994 | McKaughan et al. | 364/552 |
| 5,305,392 | 4/1994 | Longest, Jr. et al. | 382/8 |
| 5,377,279 | * 12/1994 | Hanafusa et al. | 382/141 |
| 5,440,648 | * 8/1995 | Roberts et al. | 382/141 |
| 5,566,243 | 10/1996 | Baller et al. | 382/108 |
| 5,696,591 | * 12/1997 | Bilhorn et al. | 356/238 X |
| 5,764,874 | * 6/1998 | White | 396/155 |
| 5,774,177 | * 6/1998 | Lane | 348/88 |
| 6,104,427 | * 8/2000 | Stein et al. | 348/88 X |

* cited by examiner

Primary Examiner—Howard Britton
(74) Attorney, Agent, or Firm—Beyer Weaver & Thomas, LLP (57) ABSTRACT

A web inspection apparatus (20) and method for use in identifying surface anomalies (26) on a moving material web (21) including a scanning device (22) and data processing circuitry (23) for monitoring and analyzing the output data of the scanning device (22). The scanning device (22) is configured to continuously scan a surface (25) of the moving web (21) and generates output data representative of the surface of the web. The data processing circuitry (23) is responsive to selected output data representing at least one type of surface anomaly (26) such that Region Of Interest (ROI) data are automatically recorded. This ROI data represents the detected anomaly (26) and an immediate surrounding region (27) including the detected anomaly. The hands-free data processing circuitry (23) continuously monitors and analyzes the output data generated by the scanning device (22) while the ROI data is being stored. A storage device (28) is coupled to the data processing circuitry (23) for storage of the selected ROI data.

28 Claims, 7 Drawing Sheets

VISUALIZATION SYSTEM AND METHOD FOR A WEB INSPECTION ASSEMBLY

TECHNICAL FIELD

The present invention relates, generally, to web inspection assemblies and, more particularly, relates to visualization systems for high speed, high resolution web inspection assemblies.

BACKGROUND ART

In recent years, considerable effort has been directed toward on-line web inspection to enhance the uniform quality of material webs, such as paper, glass, plastic, textiles, metallic sheets, fiberglass and sheet substrates. These web inspection assemblies are capable of high speed, high resolution detection and classification of surface imperfections in continuously manufactured products at rates in excess of 500 inches per second. Such surface imperfections include tears, through-holes, abrasions and scattering imperfections, impurities preventing local processing, stains and absorbing imperfections, pinch marks, thickness imperfections, and other far side and near side imperfections.

Web inspection assemblies often include an illumination source generating a point of light or a strip of light, and a photoelectric light sensor device or a conventional linear Charge Coupled Device (CCD) array or camera strategically positioned and angled to receive diffusely reflected light from a target surface illuminated by the generated light. Due to the scattering imperfections on or in the target surface, differences in light intensity of the reflected or transmitted light will be detected which may represent one of the above-mentioned surface imperfections. The light sensor device then delivers a signal to an electronic processing device representative of the type and magnitude of the surface imperfection.

To assure proper operation of the web inspection assembly, a visualization subsystem is often provided to format the scanner data generated by the sensor or camera device into visual form meaningful to the inspection operator. This verification tool is generally a visual image or topographic form illustrated on a display monitor.

Due to the high roll speeds of the moving web, real-time visualization of a detected anomaly is difficult to attain. Hence, the image of the defect is typically a freeze frame of the formatted scan data designated by the operator. Typically, these current visualization arrangements include real-time, remote visual inspection devices which require manual observation. Hence, these designs are relatively labor intensive to operate since the operator must devote their operative attention entirely to the viewing the monitor to identify a surface anomaly. This is true whether or not the moving web surface under inspection is good or defective. Should the operator fail to observe an anomaly on the display screen, for whatever reason, the defect may pass undetected.

Once an anomaly is visually and manually identified, some systems require the operator to manually pan or zoom in on the detected anomaly an define a region of interest to be displayed on the monitor. Subsequently, the operator must decide whether the processed image should be recorded in a storage device for retrieval at a later time. One problem associated with these systems is that the visualization techniques are performed in real-time scrolling illustrations on the monitor until a defect is identified. Subsequently, in some systems, the operator must pan or zoom in on the potential defect for viewing. During this operation, the operator must either stop or slow the moving web in order to view or mark the defect, or the operator must stop normal real-time viewing of the monitor while the web continues to move.

Stopping a high speed moving web, however, is a difficult task since the web is a continuous process manufacturing. Accordingly, the costs associated with stopping the web are substantial.

On the other hand, pausing the real-time scrolling to pan in on the defect may also be problematic since the web continues to move. Not only is this technique labor intensive, but should there be multiple defects when the operator is devoting his attention to viewing the first identified anomaly on the monitor, these other defects may pass through the visualization system undetected. Multiple tasking was not an option.

Further, visual resolution is often poor due in-part to the data compression techniques employed. To scale the entire cross-web to fit on the display monitor, the information must be reduced to the resolution of the monitor. In effect, the resolution is substantially reduced for viewing on a VGA monitor (typically 1024×768 pixels).

Finally, while some of these designs include storage devices to store records of the web inspection, the amount of storage space required to reproduce an image of a single defect is substantial since these designs are only capable of storing full frames. For example, even if a defect only measured 1×1 pixel, the full frames of 512×512 pixels would be stored in these designs. Accordingly, a substantial amount of unnecessary storage space is required, because each defect would require 262,144 bytes (i.e., 512×512).

DISCLOSURE OF INVENTION

Accordingly, it is an object of the present invention to provide a visualization subsystem and method for a web inspection assembly which operates more efficiently and in a hands-free manner.

Yet another object of the present invention is to provide a visualization subsystem and method for a web inspection assembly which automatically and selectively determines which anomalies to display on a monitor.

Still another object of the present invention is to provide a visualization subsystem and method for a web inspection assembly which increases the resolution of the anomaly on the monitor.

Another object of the present invention is to provide a visualization subsystem and method for a web inspection assembly which reduces the amount of storage space required to store an image of the detected surface anomaly.

It is a further object of the present invention is to provide a visualization subsystem and method for a web inspection assembly which can be easily retrofit to any type of line scan device, camera, laser scanner or the like.

Still yet another object of the present invention is to provide a visualization subsystem and method for a web inspection assembly which reduces operator error.

Still a further object of the present invention to provide a visualization system for a web inspection assembly which is durable, compact, easy to maintain, has a minimum number of components, cost effective to manufacture, and is easy to use by moderately skilled personnel.

In accordance with the foregoing objects, a web inspection apparatus is provided for use in identifying surface anomalies on a moving material web including a scanning device and data processing circuitry for monitoring and analyzing the output data of the scanning device. The scanning device is configured to continuously scan a surface of the moving web and generates output data representative of the surface of the web. The data processing circuitry is responsive to selected output data representing at least one type of surface anomaly such that Region Of Interest (ROI) data are automatically recorded. This ROI data represents the detected anomaly and an immediate surrounding region including the surface anomaly. Further, the data processing circuitry is configured to continuously monitor and analyze the output data generated by the scanning device while the ROI data is being stored. A storage device is also provided, coupled to the data processing circuitry, for storage of the selected ROI data.

The web inspection apparatus further includes a subsystem device operatively coupled between the scanning device and the data processing circuitry, which is adapted to process the scanning device output data for detection and location marking of the detected surface anomaly relatively along the moving material web. This subsystem device further processes the video sensor output data into two components, one of which includes a high pass filtered component.

The scanning device is adapted to scan the moving web along a width dimension thereof in a sequential line-by-line manner generating a line scan data set representative of the output data of each line scan. The data processing circuitry includes a buffer device and line delay circuitry configured to sequentially delay submission of each line scan data set to the buffer device. This submission delay is performed sequentially line-by-line by a first predetermined number of line scans which precede a current line scan being monitored and analyzed thereof. The data processing circuitry further includes line scan dilator circuitry in operable communication with the buffer device. This dilator circuitry is and adapted to activate the buffer device, in response to the real-time detection of the detected surface anomaly on the current line scan, to commence processing of each delayed line scan data set contained in the buffer device. This data processing is performed in a down-web direction for a second predetermined number of line scans to define the ROI data.

Each line scan data set is composed of a plurality of sequential pixel components representative of each line scan. Further, the data processing circuitry of the present invention includes a cross-web pixel delay circuitry configured to sequentially delay submission of each pixel component of each line scan data set to the buffer device. This pixel component submission delay is by a first predetermined number of pixel components sequentially preceding a current pixel component of the current line scan being monitored and analyzed thereof. Moreover, the data processing circuitry further includes cross-web pixel dilator circuitry in operable communication with the buffer device which is adapted to activate the buffer device, in response to the detection of the surface anomaly at the current pixel component being analyzed. Such activation commences processing of the delayed pixel components of each delayed line scan data set contained in the buffer device in a cross-web direction for a second predetermined number of pixel components to further define the ROI data.

In one embodiment of the present invention, an image of the first detected anomaly is displayed on the monitor until a second detected ROI is detected by the data processing circuitry whereby the second detected ROI displaces the first detected ROI on the display monitor.

A method of the present invention is provided for identifying surface anomalies on a moving material web including the steps of A) continuously scanning a surface of the moving web through a scanning device adapted to generate output data representative of the surface of the web; and B) analyzing the output data generated by the scanning device to detect at least one type of recognized surface anomaly. The method of the present invention further includes the step of C) upon detection of at least one type of recognized surface anomaly, constructing Region Of Interest (ROI) data representative of the detected surface anomaly and an immediate region peripherally surrounding the detected anomaly; and D) recording the ROI data in a storage device for hands-free operation thereof, while continuously analyzing the output data generated by the scanning device.

In another aspect, the method of the present invention includes the step of automatically displaying formatted ROI data on a display device. Another step includes displaying the ROI data on a display device until a second detected ROI data is detected by the data processing circuitry whereby the second detected ROI data displaces the first detected ROI data on the display device.

The scanning step may be performed by sequentially scanning the moving web along a width thereof in a sequential line-by-line manner, and generating a line scan data set representative of the output data for each line scan. The constructing step includes the step of sequentially delaying the submission of the line scan data set of each line to a buffer device by a first predetermined number of line scans which sequentially precede a current line scan being analyzed thereof. Upon real-time detection of the detected surface anomaly on the current line scan, activating the buffer device to commence processing of each delayed line scan data set contained therein in a down-web direction for a second predetermined number of line scans to define the ROI data.

In another aspect of the present invention, the constructing step further includes the step of sequentially delaying the submission of each pixel component of each line scan data set to the buffer device by a first predetermined number of pixel components sequentially preceding a current pixel component of the current line scan being analyzed thereof. Upon the real-time detection of the detected anomaly on the current pixel component, activating the buffer device to commence processing of the delayed pixel components of the delayed line scan data set in a cross-web direction for a second predetermined number of pixel components to further define the ROI data.

BRIEF DESCRIPTION OF THE DRAWING

The assembly of the present invention has other objects and features of advantage which will be more readily apparent from the following description of the best mode of carrying out the invention and the appended claims, when taken in conjunction with the accompanying drawing, in which:

BEST MODE OF CARRYING OUT THE INVENTION

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Figure 1:
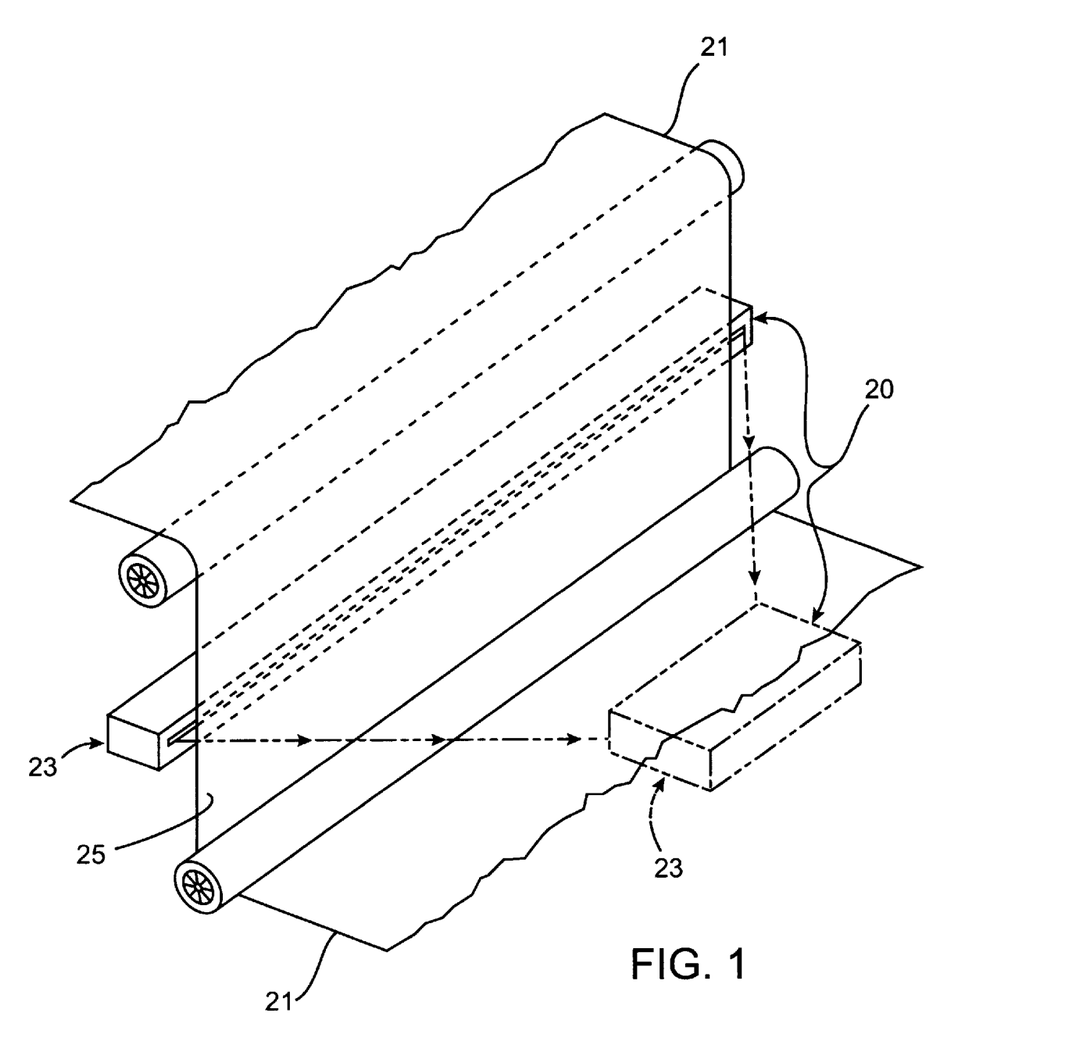
FIG. 1 is a top perspective view of a web inspection system for inspection of a material web which incorporates a visualization system constructed in accordance with the present invention.
Figure 2:
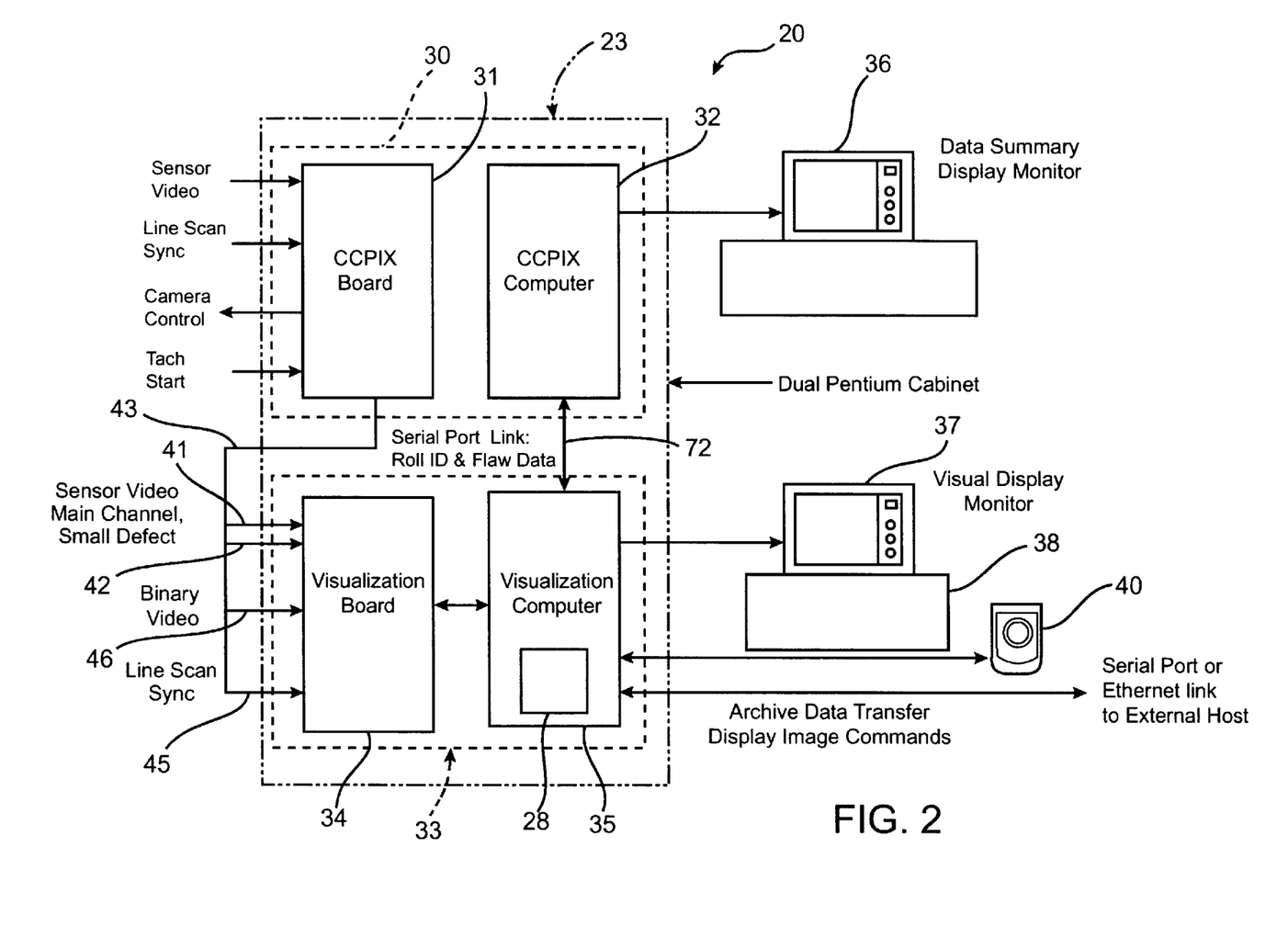
FIG. 2 is a schematic representation of the web inspection assembly incorporating the visualization system of the present invention.
Figure 3:
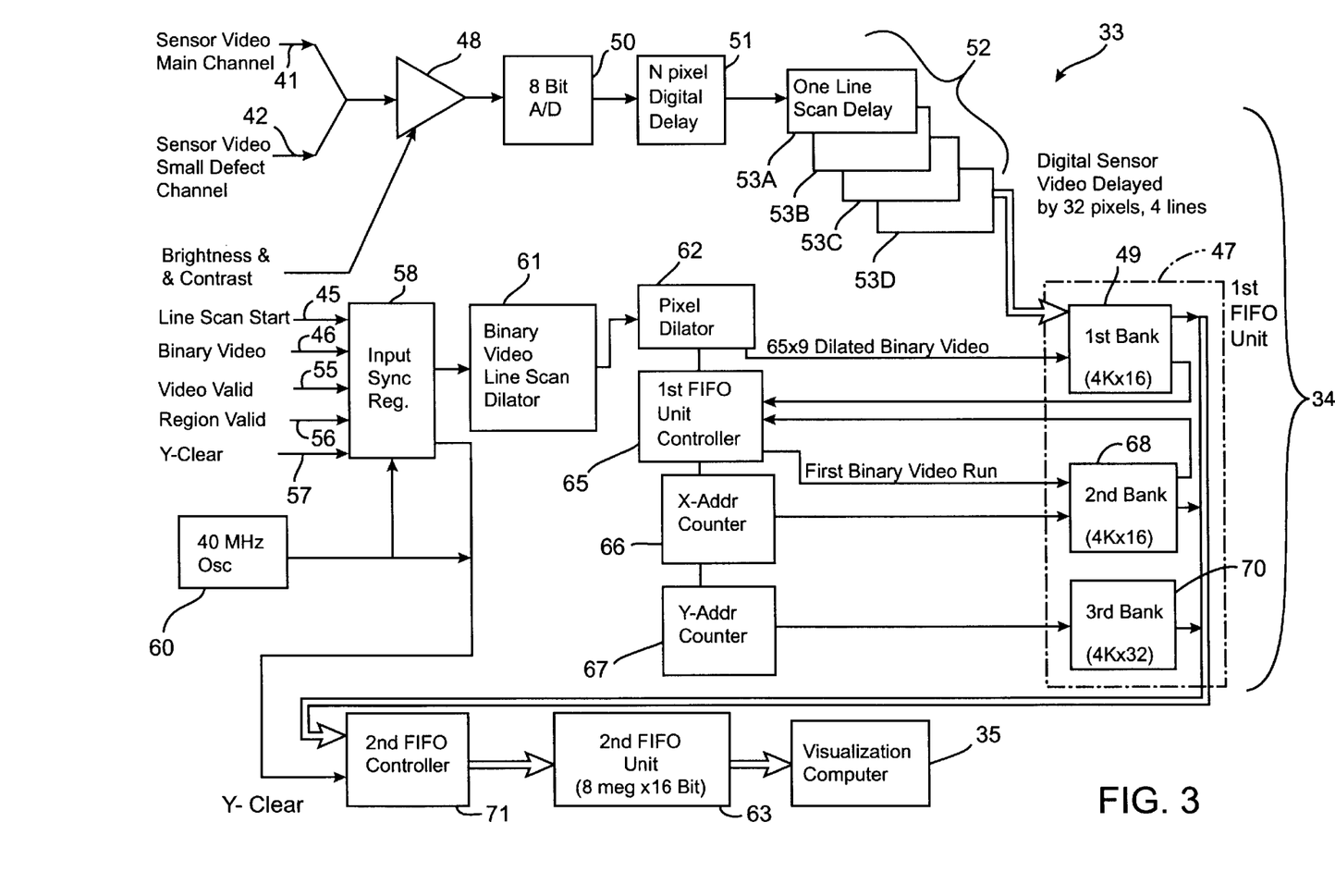
FIG. 3 is a schematic representation of the visualization system of the present invention.
Figure 4:
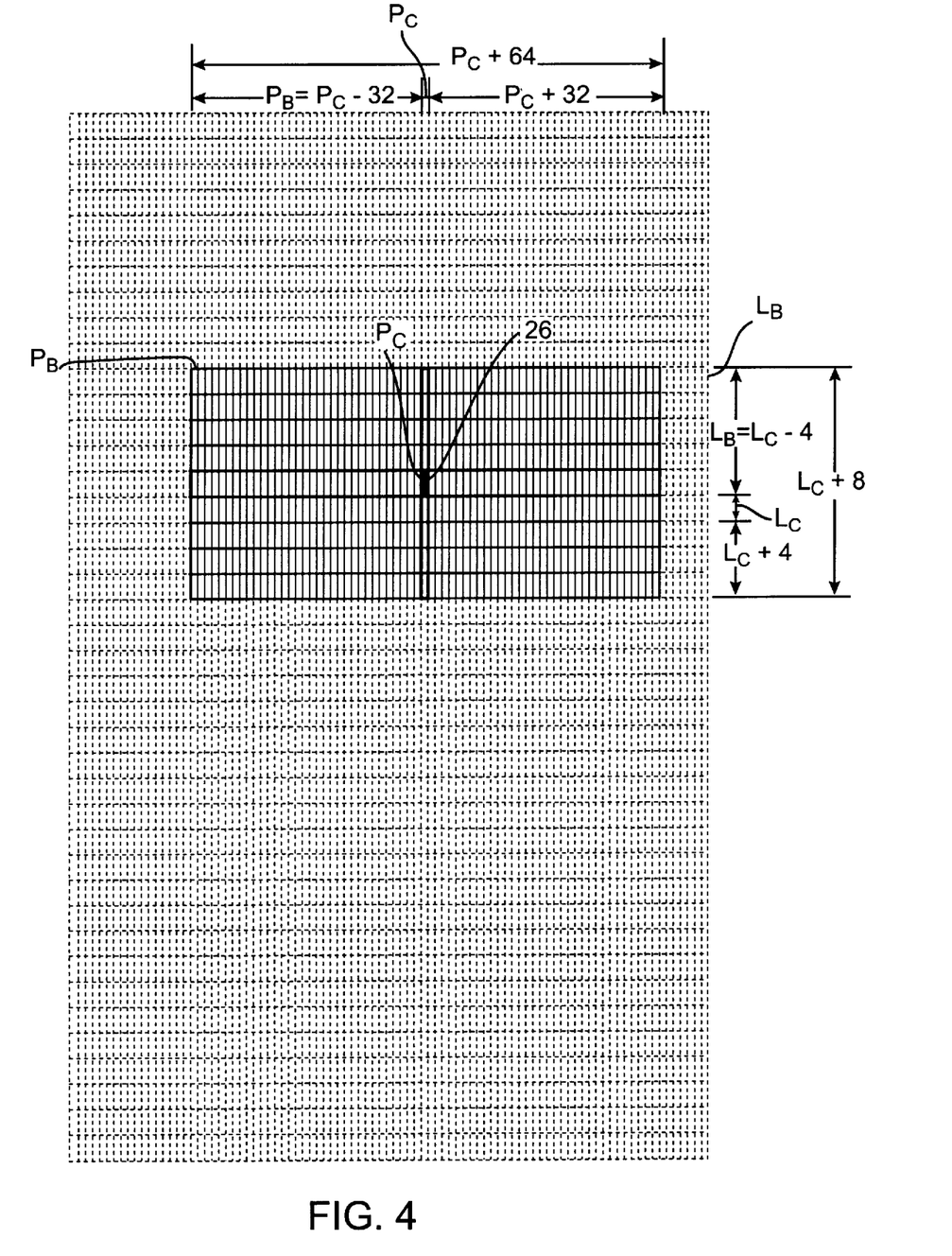
FIG. 4 is a top plan view schematic representation of an example Region Of Interest dilated peripherally around a single pixel, single line scan defect, in accordance with the visualization system of the present invention.
Figure 5:
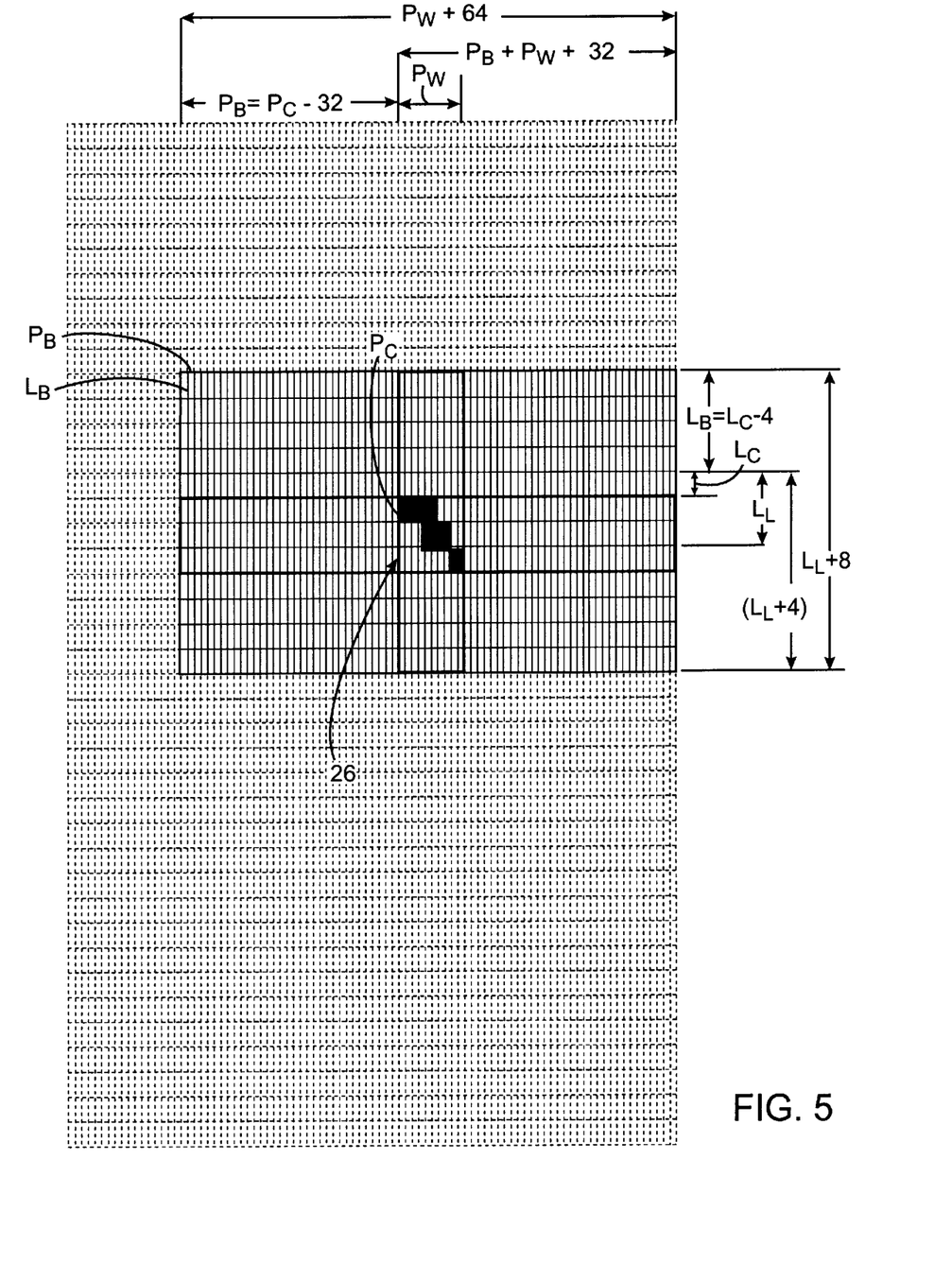
FIG. 5 is a top plan view schematic representation of another example Region Of Interest dilated peripherally around a multiple pixel, multiple line scan defect, in accordance with the visualization system of the present invention.

Attention is now directed to FIGS. 1–3 where a web inspection apparatus, generally designated 20, is illustrated for use in identifying surface anomalies on a moving material web 21. The web inspection apparatus in accordance with the present invention includes a scanning device 22 and data processing circuitry, generally designated 23, for monitoring and analyzing the output data of the scanning device 22. The scanning device is configured to continuously scan a surface 25 of the moving web 21 and generates output data representative of the surface 25 of the web 21. The data processing circuitry 23 is responsive to selected output data representing at least one type of surface defect or anomaly 26 such that formatted Region Of Interest (ROI) data (as represented in the image of FIGS. 4 and 5) are automatically recorded. This ROI data represents the detected anomaly 26 and an immediate surrounding region 27 including the surface anomaly which is formatted for viewing. Further, the data processing circuitry is configured to continuously monitor and analyze the output data generated by the scanning device while the formatted ROI data is being viewed and recorded. A storage device, generally designated 28, is also provided, coupled to the data processing circuitry, for storage of the selected ROI data.

The present invention, thus, provides a visual verification tool which cooperates with a conventional line scanner or web inspection subassembly to produce complete visualization records of selected detected defects. Unlike the prior art visualization tools which work in conjunction with web inspection devices, the present invention enables complete visualization records of simultaneous, multiple anomalies, regardless of whether the operator actually observes the anomaly.

Accordingly, the present invention enables hands-free operation of the visual verification tool without requiring constant and continuous observation and operation by the operator as the web progresses therealong at high speed rates. Since the selected anomaly is automatically recorded in the storage device and displayed on a display monitor device, the operator need not observe every detected defect on the monitor. In effect, the operator decision making is also reduced since he is not responsible for determining which defects to view and record. The operator may, thus, devote his attention to other important tasks. Multiple defect anomalies, moreover, will not pass by the screen undetected in instances where the operator may be viewing other detected anomalies on the monitor. The display maps the intensity of each pixel in the ROI to a color or gray shade on the monitor, and can be presented in a typical two dimensional or a three dimensional topological format. Moreover, post-inspection review is facilitated in a scrolling window interface. The stored ROI data can be played back in sequential order, random order, by defect type or by lane. Zooming, panning and contrast enhancement are further provided, as well as operating database functions which include histograms of flaws by cross-web lane, down-web interval and by defect type.

As will be described below, the present invention does not compress, average or delete any of the pixel data received from the scanner device, and hence, is capable of greater display resolution once the ROI data is defined. Only the ROI data is recorded of the high resolution electronic image. Hence, substantial storage space is saved by only recording the detected defect itself together with the immediate region peripherally surrounding the defect (i.e., the ROI data). In contrast the prior art systems generally store full frames of the scan data which mandate recording all areas of the web surface most of which are not affected by the targeted anomaly.

Briefly, as shown in FIG. 2, the data processing circuitry 23 of web inspection apparatus 20 includes a web inspection subsystem 30 and a visualization subsystem 33. The web inspection subsystem 30 includes a Camera Controller Pixel locator (CCPIX) board 31 and a first dedicated CCPIX computer 32. The visualization subsystem 33 includes a visualization board 34 and a second dedicated visualization computer 35. A first display monitor 36 is employed for display for the web inspection system functions, while a second display monitor 37 is provided for the ROI image display for the visualization system. A standard keyboard 38 and a mouse 40 may be used as the input device for the ROI program.

The visualization board 34 cooperates with web inspection subsystem 30 to provide visual images of the detected defects which are employed as a verification tool for the proper functioning of web inspection subsystem 30. Hence, once the web inspection subsystem 30 detects and marks the anomalous regions, the visualization board 34 selectively processes the scanner output data of the detected defect 26 to format the Region of Interest (ROI) data which in turn is displayed on a second display monitor 37 for verification purposes.

In accordance with the present invention, CCPIX board 31 is operationally coupled to the external line scanning device 22 for receipt of the line scan or sensor video output data. Other control interconnections between the CCPIX board and the line scanner may include a camera controller line, a tachometer/start line which supplies down-web location on the optional start inspection switch, and a line scan synchronization line from the external scanner which starts the line scan processing in the CCPIX board 31.

The CCPIX board 31 processes the analog sensor video output data into two-components including a main channel component 41 and a small defect component 42. The main channel component 41 is generally an amplified output signal from the line scanning device 22 which is very similar in content to the original scanner output data signal, while the small defect component 42 represents a high pass filtered version of the line scan sensor video. The high pass filter typically removes the low frequency components of the signal which include the background variations. The remaining frequencies are therefore sensitive to the rate of change of the intensity of the light. Collectively, this sensor video data signal can be formatted to provide two independent visual images of the ROI on the display screen. Preferably, however, only one signal at a time is selected for processing for use in visualization. It will be further appreciated that other conventional pass filters may be employed which may provide better resolution and/or contrast in certain instances without departing from the true spirit and nature of the present invention.

The present invention preferably maintains use of the analog sensor video data signals generated by the line scanner. This arrangement tends to be more cost effective, and reduces the number of required electrical components such as the number of analog-to-digital and digital-to-analog converters.

It will be appreciated that the present invention may be retrofit for use with conventional line scanners such as a laser, or a linear Charge Coupled Device (CCD) array or camera. The scanning device 22 is further preferably adapted to scan the moving web 21 along a width dimension thereof in a sequential line-by-line manner. For each line scan, a line scan data set is generated, composed of a plurality of sequential pixel components which cumulatively represent the sensor video output data. It will be understood, however, that for the ease of description, the term "line scan" and "line scan data set" may be used interchangeably. In the preferred form, each cross-web line scan data set is comprised of at least about a 2,500 pixel sequential stream, and may be expanded to about 16,000 pixels across, both of which provide much higher resolution of the defect 26 than the prior art compressed or averaged data.

Through internal connection 43, the visualization board 34 also receives a line scan start signal 45, and a binary video signal 46 from the CCPIX signal processor, such as the Webview Model No. 1000 series. The line scan start signal marks the start of a new line scan (i.e. a new line scan data set), while the binary video signal communicates with the visualization board 34 whether or not a defect is detected, and if detected, activates the visualization board to commence processing the data to construct the ROI data. Typically, the binary video signal is a logic one when the accompanying analog sensor video detects an anomalous event on the web such as a hole, dark spot or a sudden change in intensity. Due to electronic processing to create the binary video, the binary video defect event trails the analog video defect event by a fixed delay of a few clock cycles.

Once the CCPIX board 31 detects a predetermined anomaly, the visualization board 34 is activated through the binary video signal to begin processing the line scan data sets. This processing includes digitizing the video data signal up to a 40 MHz rate and tagging it with the type of binary video trigger. As will be described in greater detail below, the visualization board 34 expands the region of the defect 26 to include neighboring line scans and pixels to define the ROI data. Therefore, the resulting electronic image not only includes the defect 26 but also the immediate area peripherally surrounding the defect.

Briefly, using either the main channel component 41 or the small defect component 42 of the processed sensor video output data, the binary video signal 46 and the line scan start signal 45, the visualization board 34 constructs a rectangular-shaped Region Of Interest around the defect as marked by binary video. The visualization board 34 formats the data into packets with header information to permit easy reassemble of packets into displayable images on the second display monitor 37. The visualization board 34 then temporarily records the data in a packet of 16 bytes into a buffer device 47 thereon. The visualization computer 35 reads the packets and stores them on the hard disk or storage device 28 thereof into one image file to a maximum of 15 megabytes/image file.

In accordance with the present invention, the chronological construction of the ROI includes the peripherally surrounding region immediately preceding the detected defect. Hence, while the current line data scan set is being analyzed by the CCPIX board, the visualization board must be adapted to retrieve and format the preceding line scan data sets in order to construct the surrounding ROI data preceding the detected defect.

Referring now to FIGS. 3 and 4, this task is performed by delaying the submission of the line scan data sets to buffer device 47 by a first predetermined number of line scan data sets ($N_1$). Essentially, the sequential submission of the line scan data sets filtering through the buffer device 47, which is preferably provided by a First-In First-Out (FIFO) unit, are time-shifted in the down-web or Y-direction by the first predetermined number of line scans ($N_1$). Upon detection of a defect, the CCPIX board 31 triggers the visualization board 34 (via, the binary video signal 46) to commence processing the delayed ROI data filtering through the buffer device 47. This data processing continues in the down-web direction for a second predetermined number of line scan data sets ($N_2$).

Accordingly, the first predetermined number of line scans ($N_1$) determines the beginning line scan ($L_B$) of the ROI data which is based upon the current line scan ($L_C$) being evaluated by the CCPIX board 31 and which includes the detected defect. The beginning line scan ($L_B$), filtering through a first bank 49 of the first FIFO unit 47, is therefore $N_1$ line scans before the current line scan ($L_C$), simultaneously being evaluated by the CCPIX board 31. The second predetermined number of line scans ($N_2$), moreover, determines the length (in line scans) of the ROI data which is $N_2$ line scans in length after the data processing continues from the beginning line scan ($L_B$). Accordingly, to peripherally surround the detected defect 26 located at current line scan ($L_C$), the second predetermined number of line scans ($N_2$) must be greater than the first predetermined number of line scans ($N_1$).

In the preferred embodiment, the first predetermined number of line scans ($N_1$) is between about one (1) line scan and about ten (10) line scans, and more preferably about four (4) line scans. Further, the second predetermined number of line scans ($N_2$) is between about three (3) line scans and about twenty (20) line scans, and more preferably is about nine (9) line scans.

Similarly, the submission of the pixel components for each delayed line scan data set to first bank 49 of first FIFO unit 47 is also delayed a first predetermined number of pixel components ($X_1$). Hence, the image resolution can be increased in the cross-web or X-direction since the full frame of 2,500 pixels will not be required to be compressed or averaged for viewing on the second display monitor. Moreover, substantial storage space is saved as well. Again, the sequential stream submission of the pixel components of the delayed line scan data sets filtering through the first FIFO unit 47 are time-shifted in the cross-web direction by the first predetermined number of pixel components ($X_1$). Upon detection of a defect 26 at current line scan ($L_C$) and at current pixel component line scan ($P_C$) the data processing continues in the down-web direction for the second predetermined number of line scan data sets ($N_2$) and in the cross-web direction for a second predetermined number of pixel components ($X_2$) for each subsequent line scan (i.e., for $N_2$ number of line scans) in the ROI data.

Accordingly, the first predetermined number of pixel components ($X_1$) determines the beginning pixel component ($P_B$) at the beginning line scan ($L_B$) of the ROI data which is based upon the current line scan ($L_C$) and the current pixel component ($P_C$) being evaluated by the CCPIX board 31 which incidentally includes the detected defect 26. The beginning pixel component ($P_B$) is therefore on beginning line scan ($L_B$) and $X_1$ pixels before the current evaluated pixel component ($P_C$) on current line scan ($L_C$). The second predetermined number of pixel components ($X_2$), moreover, determines the width (in pixel components) of the ROI data which is $X_2$ pixel components in width after the data processing continues from beginning pixel component ($P_B$) at the beginning line scan ($L_B$). Data processing, accordingly, continues to define the rectangular-shaped ROI data for the second predetermined number ($N_2$) of line scans after the beginning line scan ($L_B$), and for the second predetermined number of pixel components ($X_2$) after the beginning pixel component ($P_B$). Again, to peripherally surround the detected defect 26 located at current pixel component ($P_C$) the second of pixel components ($X_2$) must be greater than the first predetermined number of pixel components ($X_1$).

Preferably, the first predetermined number of pixel components ($X_1$) is between about one (1) pixel component and about sixty-four (64) pixel components, and more preferably about thirty-two (32) pixel components. Further, the second predetermined number of pixel components ($X_2$) is between about three (3) pixel components and about one hundred twenty eight (128) pixel components, and more preferably is about sixty-five (65) pixel components.

While the first and second predetermined number of line scans, and the first and second predetermined number of pixel components may vary in number, collectively, they should peripherally surround the defect 26 for viewing of the immediate surrounding region 27. Further, although the preferred ROI image is rectangular in nature, any geometric shape surrounding the defect may be constructed without departing from the true spirit and nature of the present invention.

Referring back to FIG. 3, the visualization board 34 will now be described in detail. Initially, the web inspection operator can select either the main channel component 41 or the small defect component 42 for display of the anomaly depending upon which signal may be more suitable to view the anomaly for a particular material web. This is preferably selected through a software controlled switch. After the selection, the selected sensor video output data is then directed through an amplifier 48 where the brightness and contrast of the signal can also be controlled and/or modified.

The analog output data signal is converted to an eight bit quantity by an analog-to-digital converter 50. Subsequently, the processed sensor video output data from the CCPIX board 31 is delayed in the cross-web or X-direction by pixel delay circuitry 51. In the preferred embodiment, this digital pixel delay circuitry 51 is provide by a programmable video delay integrated circuit. This delays submission of the sequential stream of pixel components, in the order received from the CCPIX board, to the first bank 49 of first FIFO unit 47 by the first predetermined number of pixel components ($X_1$), preferably thirty-two (32). Moreover, since the analog-to-digital converter 50 has a pipeline delay, the actual delay of $X_1$, to produce a net delay result of preferably thirty-two (32) pixels, is approximately about twenty-eight (28) pixel components.

When digital pixel delay circuitry 51 releases a pixel component to the first bank 49 of first FIFO unit 47, the signal will be delayed by $X_1$ (preferably 32) pixel components. For example, when the current pixel component ($P_C$) is being evaluated by the CCPIX board, the delayed pixel component in the buffer device will be pixel ($P_C - X_1$) of the delayed line scan data set ($L_C$).

In a similar manner, line scan delay circuitry 52 delays submission of the line scan data sets from the CCPIX board 31 to the first bank 49 of the first FIFO unit 47 in the down-web or Y-direction. This digital line scan delay circuitry 52 is preferably provided by bank memory arrays 53A–53D which delay submission of the line scan data sets to the buffer device 47 or first FIFO unit 47 by the first predetermined number of line scan data sets ($N_1$), preferably four (4) lines. In some instances, odd and even bank memory arrays (not shown) may be employed since these type memory devices are only capable of being in a write or read mode in any one line scan. Thus, at the 40 MHz clock speed, it would be impractical to implement a read-modify-write cycle within one pixel time of 25 nanoseconds. The two bank memory arrays are then recombined for a net effect of a four line scan delay before the delayed line scan data sets are sent to the first bank 49 of first FIFO unit 47. Accordingly, when the current line scan data set ($L_C$) is being evaluated by the CCPIX board 31, the delayed line scan data set in the first FIFO unit 47 will be line scan ($L_C - N_1$).

As either analog sensor video data output data signal 41 or 42 is input through the delay circuitry 51 and 52, the line scan start signal 45, the real-time binary video signal 46, the video valid signal 55, the region valid signal 56 and the Y-clear signal 57 are simultaneously input through an input synchronizer register 58. Briefly, the video valid signal 55 performs the function of indicating when the sensor video is present and valid, while the region valid signal 56 performs the function of indicating when the web should be scanned for defects. Lastly, the Y-clear signal 57 performs the function of setting the down-web coordinate to zero. These digital input signals are synchronized to the internal 40 MHz oscillator 60 by synchronizer register 58.

Once the CCPIX board 31 detects a defect at the current pixel component ($P_C$) of the current line scan data set ($L_C$), the binary video signal is dilated or grown in the cross-web or X-direction by the second predetermined number of pixel components ($X_2$), and is dilated or grown in the down-web or Y-direction by the second predetermined number of line scan data sets ($N_2$). More specifically, as shown in FIG. 3, binary video signal 46 communicates with a line scan dilator device 61, preferably a memory array which logically ORs pixels in the same column in eight adjacent line scans, to activate the first bank 49 of first FIFO unit 47 to begin storing and formatting the sensor video output data commencing at beginning line scan data set ($L_B$) currently flowing therethrough. Similarly, binary video signal 46 communicates with a pixel component dilator device 62 to further activate the first bank 49 of first FIFO unit 47 to begin storing and formatting the sensor video output data at beginning pixel component ($P_B$) of beginning line scan data set ($L_B$).

In the preferred embodiment and as best viewed in FIG. 4, a single line scan defect is increased in down-web length by the second predetermined number of line scans ($N_2$) which is preferably about nine (9) line scan data sets starting from delayed beginning line scan data set ($L_B=L_C-4$ (i.e., the first predetermined number of line scans ($N_1$))). This creates a down-web region that is active from line scan data set $L_B$ to $L_B+8$ (line scans), exactly nine (9) line scans in length. Since the first FIFO unit 47 stores data while the dilated binary video is active, nine (9) line scan data sets (i.e., $L_C-4$ (line scans) to $L_C+4$ (line scans)) are written into first FIFO unit 47. The total net delay, thus, is one half of the down-web dilation or four (4) line scans.

Similarly, a single pixel defect 26 is increased in cross-web width by the second predetermined number of pixel components ($X_2$) which is preferably about sixty-five (65) pixels starting from delayed beginning pixel component ($P_B=P_C-32$ (i.e., the first predetermined number of pixel components ($X_1$))) which is currently being delivered to first bank 49 of first FIFO unit 47. This creates a cross-web region that is active from pixel $P_B$ to $P_B+64$ (pixels), exactly sixty-five (65) pixels wide. Since the first FIFO unit 47 stores data while the dilated binary video is active, sixty-five (65) pixel components (i.e., $P_C-32$ (pixels) to $P_C+32$ (pixels)) are written into first FIFO unit 47. The total net delay, thus, is one half of the cross-web dilation or thirty-two (32) pixels.

A single pixel, single line scan anomaly 26, therefore, is grown to a sixty-five (65) pixel cross-web width by nine (9) line scan length. This collection of pixels is the region of interest, ROI, centered around the original anomaly 26. Accordingly, a ROI surrounding a 1×1 defect, which is preferably sixty-four (64) pixels×eight (8) scan lines, will only require 192 bytes (i.e., 64×8) of storage space as opposed to 262,144 bytes (i.e., 512×512) of the prior art systems.

For multiple pixel defects 26 and multiple line scan defects 26, as exemplified in FIG. 5, the visualization board compensates to retain the same borders about the defect. Should the defect be longer than one line scan, the beginning line scan ($L_B$) for the ROI data in the down-web direction will still commence at ($L_B=L_C-4$ (line scans)). However, as shown in FIG. 5, the line scan ROI data will end at $L_C+4$ (line scans)+$L_L$, where $L_L$ is the defect's down-web line scan length. Similarly, should the defect be wider than one pixel, the beginning pixel component ($P_B$) for the ROI data in the cross-web direction will still commence at ($P_B=P_C-32$ (pixels)). The pixel component ROI data will end, however at $P_C+32$ (pixels)+$P_W$, where $P_W$ is the defect's cross-web pixel width.

Pixel dilator device 62 preferably includes a FIFO controller which provides the control signals to read and write first FIFO unit 47. As stated above, first FIFO unit 47 temporarily buffers the formatted data prior to being temporarily stored in larger second FIFO unit 63 down line.

Coupled to FIFO controller 65 is an X-address counter 66 which counts the 40 MHz clocks, while a Y-address counter 67 which counts line start pulses from line scan start signal 45. Essentially, these counters calculate the cross-web and down-web coordinates of the defect which the FIFO controller 65 bundles together with the ROI data being formatted. A second bank 68 of first FIFO unit 47 is coupled to X-address counter 66, while a third bank 70 of first FIFO unit 47 is coupled to Y-address counter 67. FIFO controller 65 also provides the control signals to read and write second 65 bank 68 and third bank 70, and to bundle the (X, Y) coordinates with the formatted ROI data. At the commencement of the inspection, the CCPIX board resets the Y-address to match the flaw data Y addresses, to be discussed below.

The first bank 49 of FIFO unit 47 processes the selected sensor video data to the formatted ROI data, and writes the data to the second FIFO unit 63 for temporary storage therein. First FIFO unit 47, however, writes at the 40 MHz rate, while it reads at a much slower rate along with the write of second FIFO unit 63. These rates are substantially slower (about 1/10 the rate or about 100 kHz–1 MHz) due to the use of a large dynamic memory array for second FIFO unit 63 (e.g., a thirty-two (32) Megabyte DRAM). The first binary video run is used to trigger a special first FIFO data sequence to store the down-web coordinate in the first FIFO.

A second FIFO controller 71 is coupled to a second FIFO unit 63 for control thereof. Once the formatted ROI data is collected in second FIFO unit 63, the visualization computer 35 runs a Read-ROI program (FIG. 7) to access the formatted ROI data in second FIFO unit 63 for display on the second display monitor 37.

In accordance with another aspect of the present invention, the CCPIX board 31 cooperates with the CCPIX computer 32 to identify a specific defect type for each defect detected by the CCPIX board 31. This conventional technique characterizes each specific defect type by size, intensity, shade of gray, etc. A number is then assigned to each defect depending upon which category the defect is identified with. Accordingly, this information may be employed to filter certain types of defects to be identified and visualized on the display monitor.

Further, at the start of an inspection, the CCPIX computer 32 sends a Roll ID to identify the new web data over a serial port link 72 between the CCPIX computer 32 and the visualization computer 35. This task is performed in part by a Read-Flaw program diagrammed in FIG. 6 which reads the serial port link 72 for inspection start data, flaw data and inspection end data generated by the CCPIX board 31. This Read-Flaw program formats a data structure with information about the next selected region of interest to display.

Figure 6:
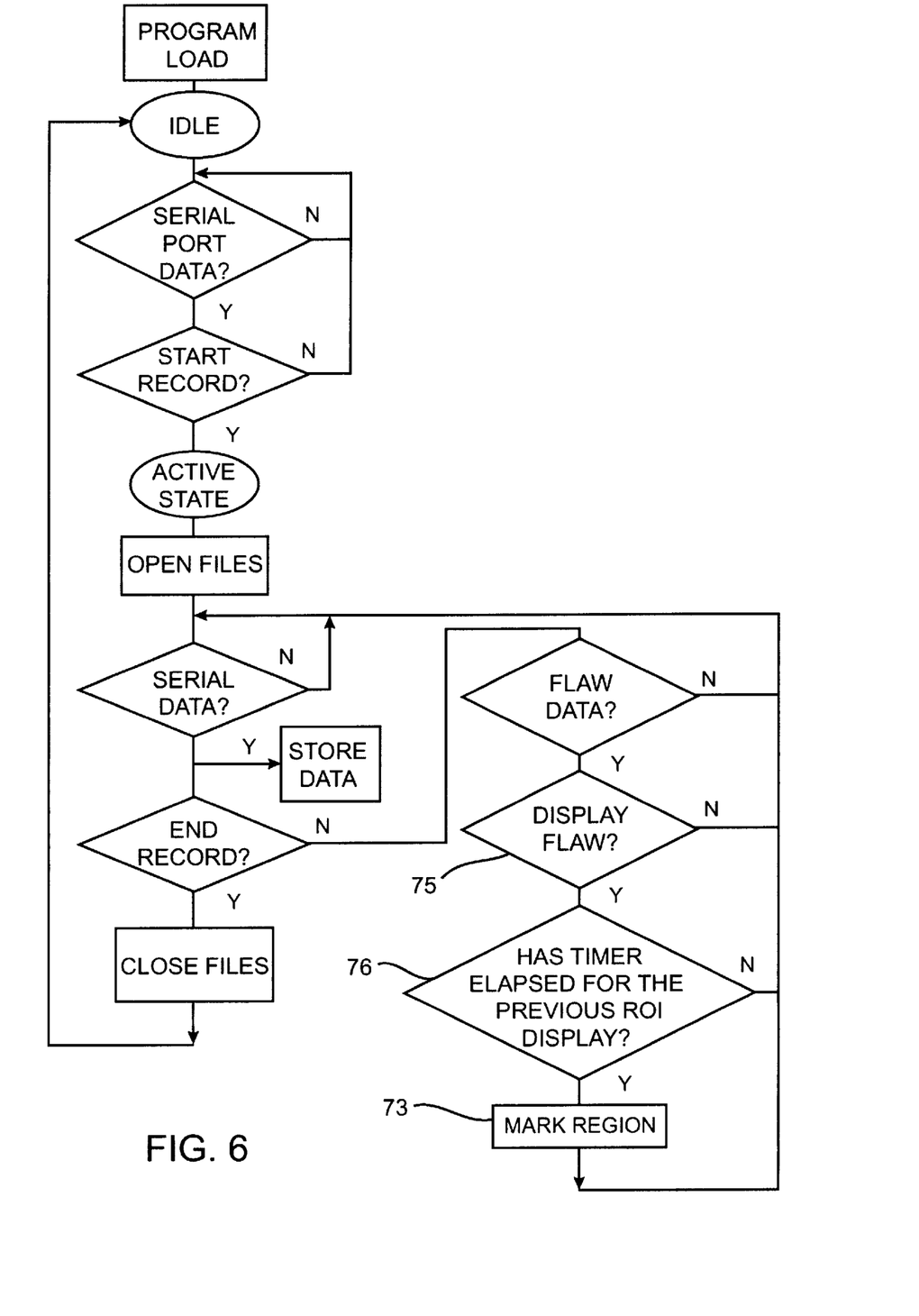
FIG. 6 is a flow diagram illustrating the steps involved in a Read-Flaw task of a CCPIX computer of the present invention.

FIG. 6 illustrated that the detected flaw is marked at step 73 for display on second display monitor 37 only when the following are true: at step 75, the flaw defect type is selected for display, and at step 76, the timer has elapsed from the previous ROI data display. If the criteria of steps 75 and 76 are not met, the detected flaw is not scheduled for display on second display monitor 37. However, all flaw data read from the serial port link and all ROI data read from the second FIFO unit 63 are in the storage device of the visualization computer 35.

The serial port link 72, which may also be provided by a dedicated parallel link to enhance throughput, further communicates the flaw records representing each anomalous object detected by the CCPIX subsystem. The visualization computer 35 queues the flaw records and waits for the ROI data corresponding to the same regions to arrive from the output of the second FIFO unit 63. This task is performed by a Read-ROI program, shown in FIG. 7, which runs concurrently with the Read-Flaw program.

Figure 7:
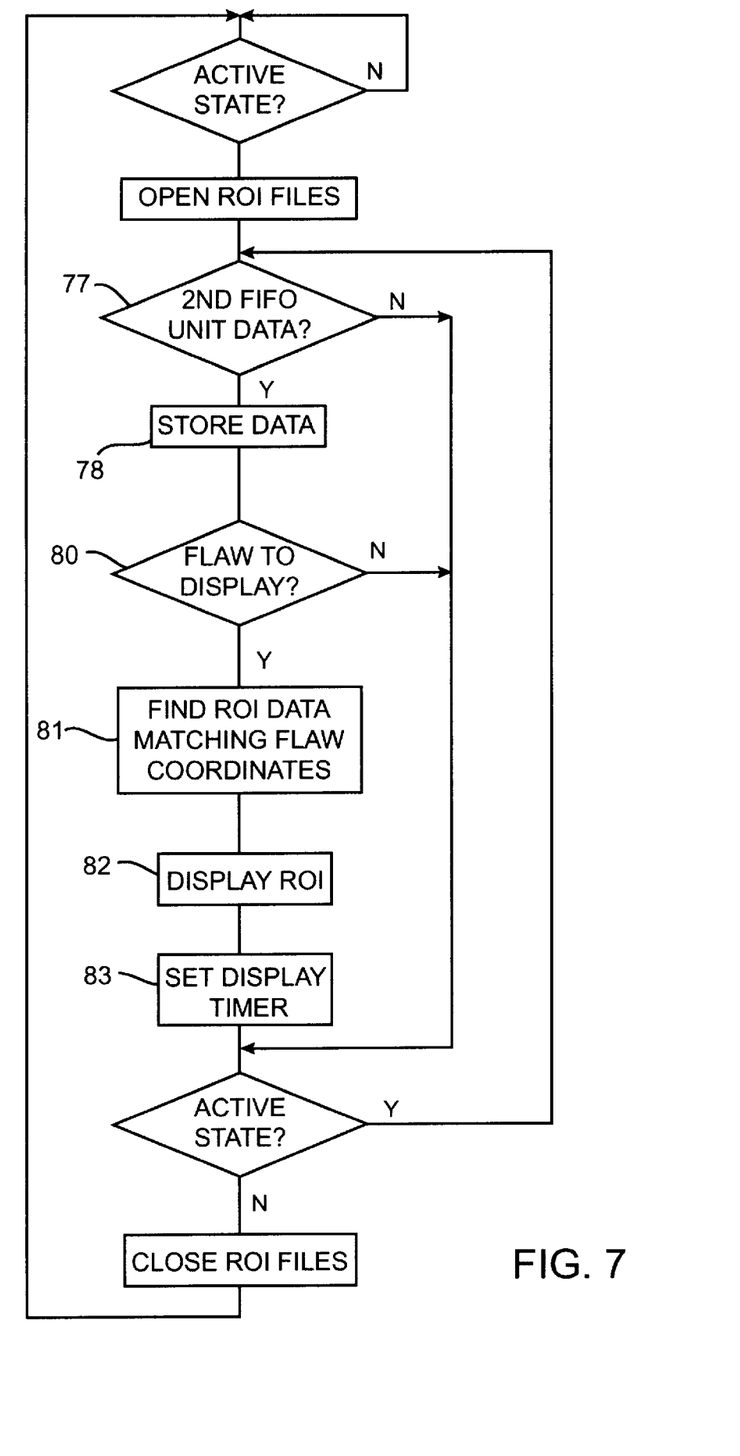
FIG. 7 is a flow diagram illustrating the steps involved in a Read-ROI task of a visualization computer of the present invention.

The Read-ROI program reads the second FIFO unit 63 for formatted ROI data at step 77 and stores the data on a disk in the visualization computer at step 78 using the operating system's stream writing service. Upon marking of a flaw for display at step 80, the Read-ROI program retrieves the matching ROI data at step 81 using the operating system's read stream service. Read-ROI then displays the formatted ROI data on the second display monitor 37 at step 82. A display timer is then set at step 83 for display of the current anomaly for a predetermined amount of time.

The Read-ROI program tags regions of the web using the flaw data and then assigns the packets of ROI data from the second FIFO unit 63 to these regions. When all of the formatted ROI data has been read for the flaw record, the visualization computer 35 formats the ROI data for display on the second display monitor 37. Simultaneously, the visualization computer stores the ROI data on disk for the post-inspection review program. Accordingly, the storing and displaying of formatted ROI data is automatic, with the display of each subsequent ROI image for a predetermined time on the second display monitor (via, the display timer) before display of the next sequential ROI image.

In another aspect and as apparent from the description of the present invention, a method is provided for identifying surface anomalies on a moving material web 21 including the steps of A) continuously scanning a surface of the moving web 21 through a scanning device 22 adapted to generate output data representative of the surface of the web; and B) analyzing the output data generated by the scanning device 22 to detect at least one type of recognized surface anomaly 26. The method of the present invention further includes the step of C) upon detection of at least one type of recognized surface anomaly, constructing Region Of Interest (ROI) data representative of the detected surface anomaly 26 and an immediate region 27 peripherally surrounding the detected anomaly 26; and D) recording the ROI data in a storage device 28 for hands-free operation thereof, while continuously analyzing the output data generated by the scanning device 22.

The method further includes the step of automatically displaying formatted ROI data on second display monitor or device 37. Another step includes displaying the ROI data on second display monitor until a second detected ROI data is detected by the data processing circuitry 23 whereby the second detected ROI data displaces the first detected ROI data on the display monitor.

The scanning step may be performed by sequentially scanning the moving web 21 along a width dimension thereof in a sequential line-by-line manner, and generating a line scan data set representative of the output data for each line scan. The constructing step further includes the step of sequentially delaying the submission of the line scan data set of each line to a buffer device 47 by a first predetermined number of line scans ($N_1$) which sequentially precede a current line scan ($L_C$) being analyzed thereof. Upon real-time detection of the detected surface anomaly on the current line scan ($L_C$), activating the buffer device 47 to commence processing of each delayed line scan data set ($L_B$) contained therein in a down-web direction for a second predetermined number of line scans ($N_2$) to define the ROI data.

In another aspect of the present invention, the constructing step further includes the step of sequentially delaying the submission of each pixel component of each line scan data set to the buffer device 47 by a first predetermined number of pixel components ($X_1$) sequentially preceding a current pixel component ($P_C$) of the current line scan ($L_C$) being analyzed thereof. Upon the real-time detection of the detected anomaly 26 on the current pixel component ($P_C$), activating the buffer device 47 to commence processing of the delayed pixel components ($P_B$) of the delayed line scan data set ($L_B$) in a cross-web direction for a second predetermined number of pixel components ($X_2$) to further define the ROI data.

What is claimed is:

1. A web inspection apparatus for use in identifying surface anomalies on a moving material web comprising:
   a scanning device configured to continuously scan a surface of the moving web, said scanning device generating output data representative of the surface of the web;
   data processing circuitry for monitoring and analyzing the output data, and responsive to selected output data representing at least one type of surface anomaly such that Region Of Interest (ROI) data, including the detected anomaly and an immediate region including the surface anomaly, are recorded while continuously monitoring and analyzing the output data generated by the scanning device; and
   a storage device coupled to the data processing circuitry for storage of the selected ROI data.

2. The web inspection apparatus according to claim 1 further including:
   a subsystem device operatively coupled between the scanning device and the data processing circuitry, and adapted to process the scanning device output data for detection and location marking of the detected surface anomaly relatively along the moving material web.

3. The web inspection apparatus according to claim 2 wherein,
   said subsystem device is adapted to process the received output data into a two component input data.

4. The web inspection apparatus according to claim 3 wherein,
   said two component input data includes a high pass filtered component.

5. The web inspection apparatus according to claim 1 wherein,
   said data processing circuitry is configured to display the ROI data on a display device until a second detected ROI is detected by the data processing circuitry whereby the second detected ROI displaces the first detected ROI on the display device.

6. The web inspection apparatus according to claim 1 wherein,
   said scanning device is adapted to scan the moving web along a width dimension thereof in a sequential line-by-line manner generating a line scan data set representative of the output data of each line scan.

7. The web inspection apparatus according to claim 1 wherein,
   said data processing circuitry includes:
   a buffer device, and
   line delay circuitry configured to sequentially delay submission of each line scan data set to the buffer device by a first predetermined number of line scans sequentially preceding a current line scan being monitored and analyzed thereof.

8. The web inspection apparatus according to claim 7 wherein,
   said data processing circuitry further includes line scan dilator circuitry in operable communication with the buffer device, and adapted to activate the buffer device, in response to the real-time detection of said detected surface anomaly on the current line scan, to commence processing of each delayed line scan data set contained in the buffer device in a down-web direction for a second predetermined number of line scans to define the ROI data.

9. The web inspection apparatus according to claim 8 wherein,
the first predetermined number of line scans is between about one line scan and about ten line scans.

10. The web inspection apparatus according to claim 9 wherein,
the first predetermined number of line scans is about four line scans.

11. The web inspection apparatus according to claim 8 wherein,
the second predetermined number of line scans is between about three line scans and about twenty scan-lines.

12. The web inspection apparatus according to claim 11 wherein,
the second predetermined number of line scans is about nine line scans.

13. The web inspection apparatus according to claim 8 wherein,
said line delay circuitry includes a memory array each formed to retain a line scan data set of a respective line scan for said first predetermined number of line scans.

14. The web inspection apparatus according to claim 13 wherein,
said buffer device includes a first-in-first-out memory controller.

15. The web inspection apparatus according to claim 14 wherein,
each line scan data set is composed of a plurality of sequential pixel components representative of each line scan, and
said data processing circuitry further includes a cross-web pixel delay circuitry configured to sequentially delay submission of each pixel component of each line scan data set to the buffer device by a first predetermined number of pixel components sequentially preceding a current pixel component of said current line scan being monitored and analyzed thereof.

16. The web inspection apparatus according to claim 15 wherein,
said data processing circuitry further includes cross-web pixel dilator circuitry in operable communication with the buffer device, and adapted to activate the buffer device, in response to the detection of the surface anomaly at the current pixel component being analyzed, to commence processing of the delayed pixel components of each delayed line scan data set contained in the buffer device in a cross-web direction for a second predetermined number of pixel components to further define the ROI data.

17. The web inspection apparatus according to claim 16 wherein,
said ROI data includes the output data relating to the region immediately surrounding the detected surface anomaly.

18. The web inspection apparatus according to claim 15 wherein,
the first predetermined number of line scans is between about one line scan and about ten line scans,
the second predetermined number of line scans is between about one line scan and about ten line scans,
the first predetermined number of pixel components is between about one pixel component and about sixty-four pixel components, and,
the second predetermined number following pixel components is between about three pixel components and about one-hundred twenty eight pixel components.

19. The web inspection apparatus according to claim 18 wherein,
the first predetermined number of line scans is about four line scans,
the second predetermined number of line scans is about nine line scans,
the first predetermined number pixel components is about thirty-two pixel components, and
the second predetermined number pixel components is about sixty-five pixel components.

20. The web inspection apparatus according to claim 1 wherein,
said data processing circuitry is adapted to automatically store the ROI data for recall.

21. A method for identifying surface anomalies on a moving material web comprising the steps of:
continuously scanning a surface of the moving web through a scanning device adapted to generate output data representative of the surface of the web;
analyzing the output data generated by the scanning device to detect at least one type of recognized surface anomaly;
upon detection of at least one type of recognized surface anomaly, constructing Region Of Interest (ROI) data representative of the detected surface anomaly and an immediate region peripherally surrounding the detected anomaly; and
recording the ROI data in a storage device for hands-free operation thereof, while continuously analyzing the output data generated by the scanning device.

22. The method for identifying surface anomalies as defined in claim 21 further including the step of:
automatically displaying formatted ROI data on a display device.

23. The method for identifying surface anomalies as defined in claim 22 wherein,
displaying the ROI data on a display device until a second detected ROI data is detected by the data processing circuitry whereby the second detected ROI data displaces the first detected ROI data on the display device.

24. The method for identifying surface anomalies as defined in claim 21 wherein,
said scanning step is performed by sequentially scan the moving web along a width thereof in a sequential line-by-line manner, and
generating a line scan data set representative of the output data for each line scan.

25. The method for identifying surface anomalies as defined in claim 24 wherein,
said constructing step includes the step of sequentially delaying the submission of the line scan data set of each line to a buffer device by a first predetermined number of line scans which sequentially precede a current line scan being analyzed thereof; and
upon real-time detection of the detected surface anomaly on the current line scan, activating the buffer device to commence processing of each delayed line scan data set contained therein in a down-web direction for a second predetermined number of line scans to define the ROI data.

26. The method for identifying surface anomalies as defined in claim 25 wherein,
the first predetermined number of line scans is between about one line scan and about ten line scans, and the second predetermined number of line scans is between about three line scans and about twenty.

27. The method for identifying surface anomalies as defined in claim 26 wherein, the first predetermined number of line scans is about four line scans, and the second predetermined number of line scans is about nine line scans.

28. The method for identifying surface anomalies as defined in claim 21 wherein, each line scan data set is composed of a plurality of sequential pixel components representative of each line scan, said constructing step further includes the step of sequentially delaying the submission of each pixel component of each line scan data set to the buffer device by a first predetermined number of pixel components sequentially preceding a current pixel component of said current line scan being analyzed thereof; and upon said real-time detection of said detected anomaly on the current pixel component, activating the buffer device to commence processing of the delayed pixel components of the delayed line scan data set in a cross-web direction for a second predetermined number of pixel components to further define the ROI data.

* * * * *